United States Patent [19]

Urso

[11] Patent Number: 5,722,440
[45] Date of Patent: Mar. 3, 1998

[54] BITE DEVICE FOR DRIVING FLOSS THROUGH TIGHT INTERDENTAL GAPS

[75] Inventor: Charles L. Urso, Waltham, Mass.

[73] Assignee: DynaProducts, Inc., Nashua, N.H.

[21] Appl. No.: 621,239

[22] Filed: Mar. 25, 1996

[51] Int. Cl.⁶ .................................................. A61C 15/04
[52] U.S. Cl. ................................................................ 132/323
[58] Field of Search ............................ 132/323, 324, 132/325, 326, 327, 322; 433/140, 93, 6

[56] References Cited

U.S. PATENT DOCUMENTS

| | | | |
|---|---|---|---|
| 1,180,620 | 4/1916 | Stuart | 132/324 |
| 2,467,221 | 4/1949 | Pastl | |
| 2,872,930 | 2/1959 | Patterson | 132/324 |
| 3,421,524 | 1/1969 | Waters | |
| 3,534,745 | 10/1970 | Waters | |
| 3,667,483 | 6/1972 | McCabe | |
| 3,759,274 | 9/1973 | Warner | |
| 3,799,177 | 3/1974 | Bragg | |
| 3,847,167 | 11/1974 | Brien | |
| 3,847,168 | 11/1974 | Schlegel | |
| 3,886,956 | 6/1975 | Cash | |
| 4,014,354 | 3/1977 | Garrett | |
| 4,214,598 | 7/1980 | Lee | 132/325 |
| 4,235,253 | 11/1980 | Moore | |
| 4,245,658 | 1/1981 | Lecouturier | |
| 4,253,477 | 3/1981 | Eichman | 132/323 |
| 4,307,740 | 12/1981 | Florindez et al. | |
| 4,326,549 | 4/1982 | Hinding | |
| 4,338,957 | 7/1982 | Meibauer | |
| 4,458,702 | 7/1984 | Grollimund | |
| 4,586,521 | 5/1986 | Urso | |
| 4,605,025 | 8/1986 | McSpadden | |
| 4,706,695 | 11/1987 | Urso | |
| 4,880,382 | 11/1989 | Moret et al. | |
| 5,000,684 | 3/1991 | Odrich | |
| 5,016,660 | 5/1991 | Boggs | |
| 5,038,806 | 8/1991 | Ewald | 132/324 |
| 5,069,233 | 12/1991 | Ritter | |
| 5,176,157 | 1/1993 | Mazza | |
| 5,323,796 | 6/1994 | Urso | |

Primary Examiner—Todd E. Manaham
Assistant Examiner—E. Robert
Attorney, Agent, or Firm—Brooks & Kushman P.C.

[57] ABSTRACT

A bite device for dental flossers having a fork which supports a floss span between tines of the fork. The bite device includes a bite member (10) having a bite surface (21) on one side and a stop guard (24) on an opposite side. The bite member is movably supported between the fork tines such that the member and the fork can move up and down relative to each other. The member is connected to the fork such that a user biting on the bite surface can drive the floss span through a tight interdental gap wherein the stop guard engages a user tooth adjacent the floss span to prevent over-travel of the span thereby preventing floss impact against user gums. When the bite is released, the bite member moves to a neutral position to allow a full range of flossing motion.

21 Claims, 2 Drawing Sheets

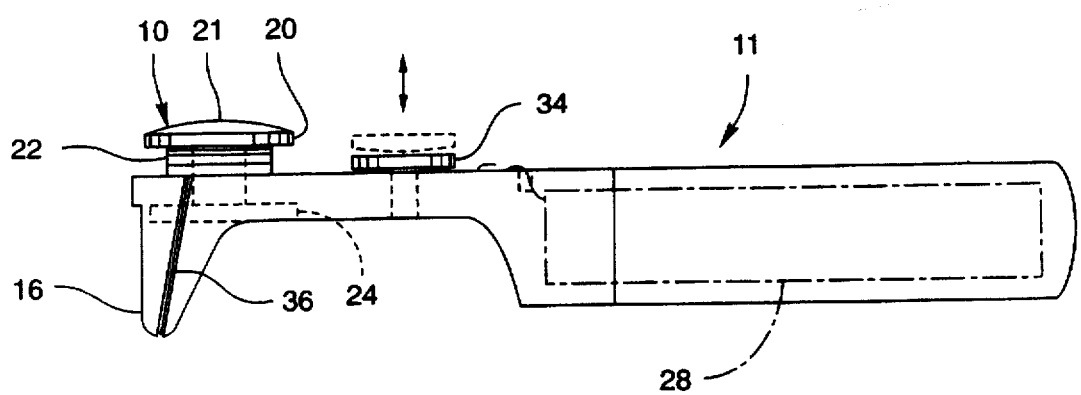
FIG. 1
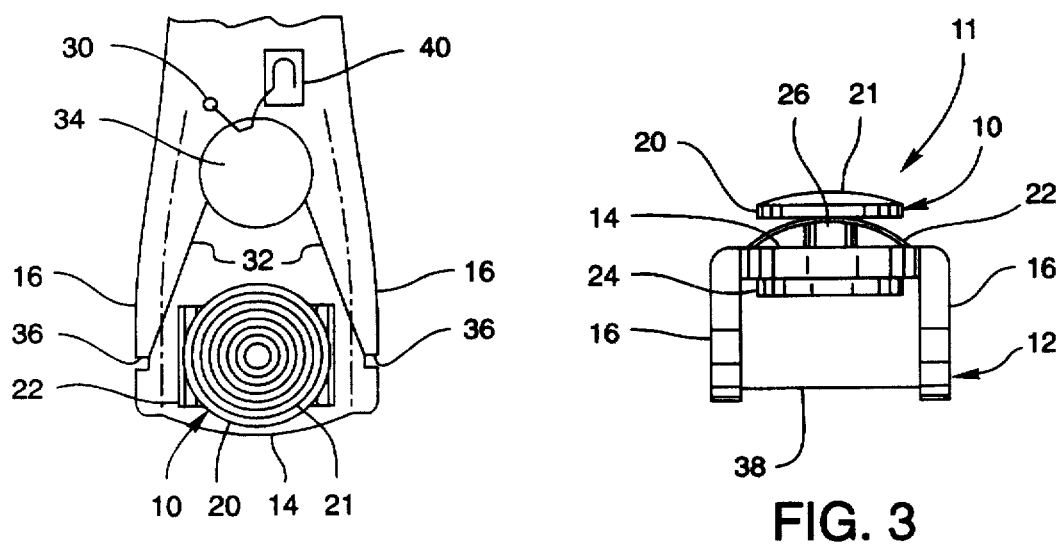
FIG. 2
FIG. 3
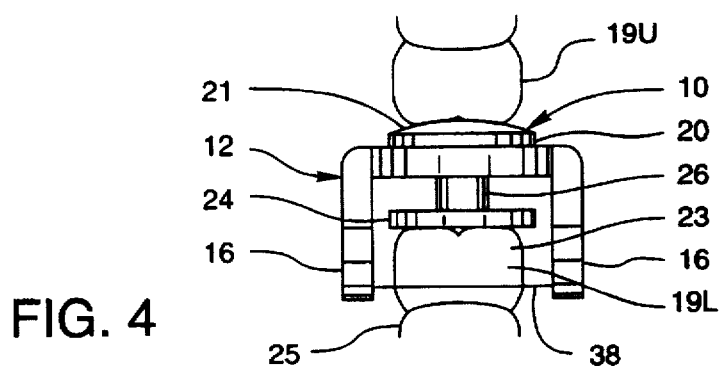
FIG. 4

BITE DEVICE FOR DRIVING FLOSS THROUGH TIGHT INTERDENTAL GAPS

TECHNICAL FIELD

This invention relates to dental flossing devices and more particularly to devices for driving floss through tight interdental gaps.

BACKGROUND

Several types of dental flossers have been introduced to the market in recent years. The flossers generally comprise a frame having a fork for supporting a span of floss between the fork tines. Most flossers are hand-operated, others are motor-driven.

A common problem with nearly all conventional flossers is that they have difficulty passing fork-held floss through tight gaps between adjacent teeth. Often, the fork cannot be adequately leveraged from outside the mouth to force a floss span through tight interdental gaps.

SUMMARY

The present invention provides a bite device for dental flossers which have a fork with tines for supporting a floss span therebetween. The bite device includes a bite member which has a bite surface on one side and a stop guard surface on an opposite side. The bite member is movably supported between the fork tines to allow a fixed amount of up and down movement of the bite member and the fork relative to each other such that a user biting on the bite surface causes the bite member to force the fork to drive the floss span through a tight interdental gap.

In preferred embodiments, the bite member is positioned relative to the fork such that when a user biting on the bite member forces the floss span through an interdental gap, the stop guard surface engages a tooth adjacent to the floss span to prevent over-travel of the span. This prevents floss impact against user gums. The bite member is movable between a neutral position and a fork-driving position. The bite member, when in the neutral position, is sufficiently distant from distal ends of the tines to allow unimpeded flossing of teeth at the user's gum line. When the bite member is in the fork-driving position, the bite member is sufficiently close to the tine distal end portions to prevent floss contact with user gums, thereby preventing gum injury from over-travel of the fork. The bite member is preferably urged to the neutral position by a leaf spring and can be either slidably or pivotably supported.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale.

FIG. 1 is a side view of a hand-operated flosser including a bite device.

FIG. 2 is a fragmented top view of the flosser of FIG. 1.

FIG. 3 is a fragmented front end view of the flosser of FIG. 1.

FIG. 4 is a fragmented front end view of the flosser of FIG. 1 in use.

DETAILED DESCRIPTION OF PREFERRED EMBODIMENTS

Figure 5:
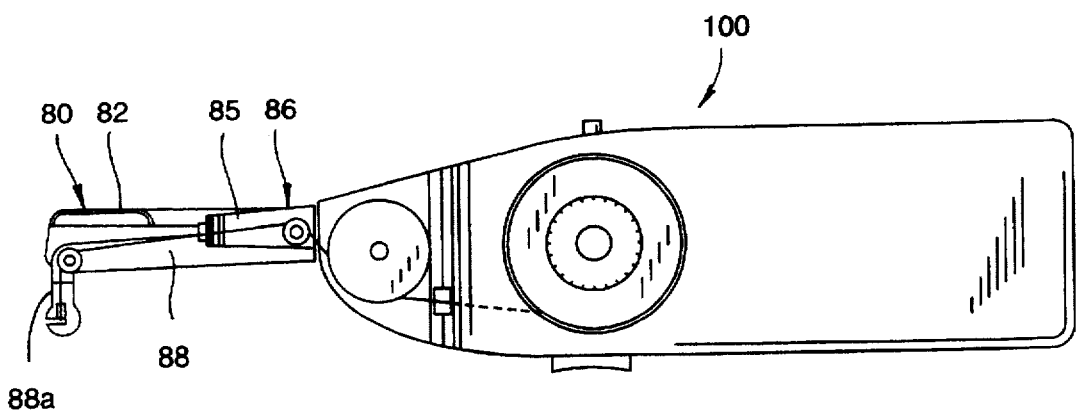
FIG. 5 is a side view of a motor-driven flosser including another preferred bite device.

Preferred embodiments of a bite device for dental flossers embodying the principles of the present invention is illustrated in the figures. The bite device can be incorporated in most flossers, including those that are motor-driven. The embodiment shown in FIGS. 1–4 is adapted to a typical hand-operated flosser 11 for illustration.

The flosser 11 includes a fork 12 (FIG. 3) molded along with a bridge 14 connecting the top edges of fork tines 16. A bite member 10 includes a bite button 20 which is supported above bridge 14 and is normally held in an up or neutral position by an arcuate leaf spring 22. A bite surface 21 of the bite member 10 is inscribed with concentric circles (FIG. 2) to make the bite surface 21 slip-resistant.

Connected to the bite button 20 is a wafer-shaped stop guard 24 (FIGS. 3 and 4) positioned below bridge 14 and between the tines 16. The stop guard 24 is spaced from the bite button 20 and is fixedly connected to the latter by a stem 26 (FIG. 3) which slidably passes through an aperture in bridge 14 and leaf spring 22. Thus, bite member 10 includes bite button 20 and stop guard 24 which are connected together by stem 26 to form a one-piece unit resembling a miniature spool.

Bite member 10 is vertically movable, relative to fork 12, between the neutral position (FIGS. 1 and 3) and a fork-driving position (FIG. 4). In the fork-driving position, bite member 10 is sufficiently close to the distal ends of fork tines 16 to prevent floss contact with user gums, thereby preventing gum injury from over-travel of fork 12 when bite-driven.

Flosser 11 (FIG. 1) includes a hollow handle with houses a floss spool 28. A port 30 (FIG. 2) allows floss 32 from spool 28 to exit from the handle, wrap around a floss tensioning button 34, extend down a tine groove 36 in one tine 16 (FIG. 1 and 2), form a floss span 38 between tines 16 (FIG. 3), extend up opposite tine groove 36 in the other tine 16 (FIG. 2), and wrap around button 34. A cutting blade 40 is provided to cut away used floss.

When a user encounters an unusually tight interdental gap, he or she can simply bite on bite button 20, thereby pushing bite button 20 to the fork-driving position. As illustrated in FIG. 4, a user's upper tooth 19U engages the bite surface 21 of bite member 10 as the user bites down. The bite-driven bite button 20 flattens leaf spring 22 and drives fork 12 downward wherein floss span 38 is forced through the tight gap 23. Simultaneously, the stop guard 24 is pushed down and its bottom surface engages the top of the user's lower tooth 19L that is adjacent floss span 38. Thus, stop guard 24 of the bite member 10 limits the depth of the floss between teeth to prevent floss span 38 from impacting the gums 25. Hence, there is no danger of trauma to gums, regardless of how hard the user bites down.

As the user releases the bite, leaf spring 22 lifts bite member 10 back to the neutral position. Bite member 10 in the neutral position is sufficiently distant from distal ends of tines 16 so as not to impede the flossing of teeth near and at the user's gum line. Thus, the user can then floss down to the gums 25 (attached gingiva) without being impeded by stop guard 24. Flossing the upper teeth is performed in a manner similar to that described above.

Figure 6:
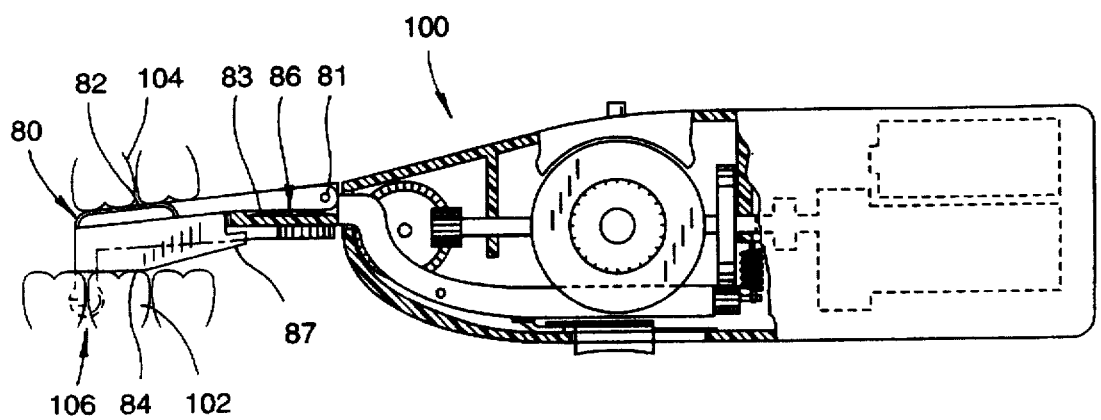
FIG. 6 is a cross-sectional view taken vertically along the longitudinal center line of the flosser of FIG. 5.
Figure 7:
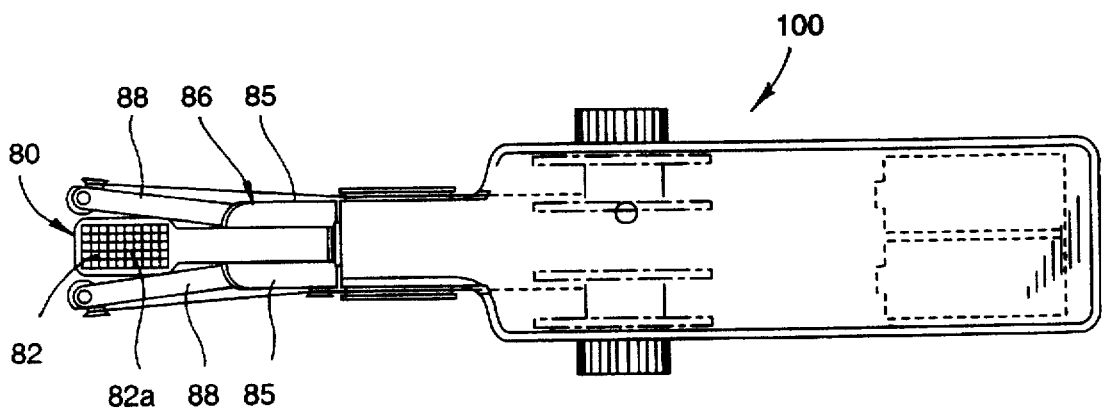
FIG. 7 is a top view of the flosser of FIG. 5.

Another preferred bite device for dental flossers is illustrated in FIGS. 5–7. The bite device is adapted to a motorized self-guiding flosser 100 similar to that described in U.S. Patent Application Ser. No. 08/572051 filed Dec. 14, 1995 which is incorporated herein by reference in its entirety.

Even without the addition of the bite device, flosser 100 is designed to effectively pass a floss span through tight interdental gaps. It does so by closing its tines 88 onto target teeth and pulling the floss through the gap in a saw-like motion. However, situations might arise in which some additional assistance is desirable. Bite member 80 is therefore provided.

The bite member 80 includes a paddle-shaped upper portion having an upper bite surface 82 (FIGS. 5 and 7). Bite surface 82 includes a thin rubber pad 82a cemented within a rectangular recess in the top of the member. Grooves forming a grid in rubber pad 82a make the bite surface 82 slip-resistant.

Extending downward from the upper portion of bite member 80 is a narrower lower portion having a lower stop guard surface 84 (FIG. 6). The lower portion is narrower in order to fit between tines 88 when the tines 88 are in a closed position.

Bite member 80 includes a posterior end portion pivotally connected between walls 85 of a pivot base 86 (FIG. 7). The bite member 80 pivots about a pin 81 (FIG. 6) which passes horizontally through walls 85 and through the upper portion of bite member 80 positioned between walls 85. Bite member 80 can pivot between a neutral position (FIG. 5) and a fork-driving position (FIG. 6). In the neutral position, a tab 87, extending from the lower portion of bite member 80, contacts the underside of pivot base 86 and prevents bite member 80 from pivoting above that position. Bite member 80 is urged toward the neutral position by an arcuate leaf spring 83 (shown flattened in FIG. 6) positioned between the bite member 80 and a slightly recessed floor of pivot base 86. When bite member 80 is in the fork-driving position, leaf spring 83 is flattened out.

In the fork-driving position, bite member 80 is engaged with the floor of pivot base 86. Thus, bite member 80, pivot base 86, and tines 88 are in rigid contact when a vertical force is applied to the bite surface 82. Therefore, if a user encounters a very tight gap 106 between teeth that is difficult to get through, the user can bite on bite surface 82 of bite member 80. With the aid of the user's jaw, the combination is leveraged to drive the floss span through the tight gap 106 with relative ease.

The stop guard surface 84 (FIG. 6) of bite member 80 in the fork-driving position is about halfway between the floss span and the horizontal legs of the fork tines 88. After the floss span passes through the tight gap 106, stop guard surface 84 engages a user's tooth 102 (FIG. 6) opposite the tooth 104 that bites the bite surface, thereby safely limiting the depth that the floss span can reach between teeth. Hence, the span cannot be driven into user gums by over-travel due to an excessive or over-zealous user bite.

After release of the bite, the bite member 80 is urged by leaf spring 83 back to the neutral position (FIG. 5) thereby exposing the vertical legs 88a of the fork tines 88 so the user can floss down to the gums without being impeded by stop guard 84. As result, flossing down to the gingival sulcus can proceed.

While the above description contains many specificities, these should not be construed as limitations on the scope of the invention, but rather as an exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. A bite device and dental flosser having a fork with spaced tines for supporting a floss span therebetween, the bite device and dental flosser comprising a bite member having a bite surface on one side and a stop guard surface on an opposite side, the bite member being movably supported between the tines to allow a fixed amount of up and down movement of the bite member and the fork relative to each other such that a user biting on the bite surface causes the bite member to force the fork to drive the floss span through a tight interdental gap, wherein the bite member is positioned relative to the fork such that when a user biting on the member forces the floss span through an interdental gap the stop guard surface engages a user tooth adjacent the floss span to prevent over-travel of the span thereby preventing floss impact against user gums.

2. The device as defined in claim 1, wherein the bite member is movable between a neutral position and a fork-driving position, the bite member in the neutral position being sufficiently distant from distal ends of the tines to allow unimpeded flossing of teeth at the user gum line, the bite member in the fork-driving position being sufficiently close to distal ends of the tines to prevent floss contact with user gums thereby preventing gum injury from over-travel of the fork.

3. The device as defined in claim 1, wherein the bite member is slidably supported.

4. The device as defined in claim 1, wherein the bite member is pivotally supported.

5. A bite device and dental flosser having a fork with spaced tines for supporting a floss span therebetween, the bite device and dental flosser comprising a bite member having a bite surface on one side and a stop guard surface on an opposite side, the bite member being movably supported between the tines to allow a fixed amount of up and down movement of the bite member and the fork relative to each other such that a user biting on the bite surface causes the bite member to force the fork to drive the floss span through a tight interdental gap, wherein the bite member is movable between a neutral position and a fork-driving position, the bite member in the neutral position being sufficiently distant from distal ends of the tines to allow unimpeded flossing of teeth at the user gum line, the bite member in the fork-driving position being sufficiently close to distal ends of the tines to prevent floss contact with user gums thereby preventing gum injury from over-travel of the fork, wherein the bite member is urged to the neutral position by a spring.

6. The device as defined in claim 5, wherein the bite member is pivotally supported.

7. The device as defined in claim 5, wherein the bite member is slidably supported.

8. A bite device and dental flosser having a fork with spaced tines for supporting a floss span therebetween, the bite device and dental flosser comprising a bite member having a bite surface on one side and a stop guard surface on an opposite side, the bite member being movably supported between the tines to allow a fixed amount of up and down movement of the bite member and the fork relative to each other such that a user biting on the bite surface causes the bite member to force the fork to drive the floss span through a tight interdental gap, wherein the bite member is movable between a neutral position and a fork-driving position, the bite member in the neutral position being sufficiently distant from distal ends of the tines to allow unimpeded flossing of teeth at the user gum line, the bite member in the fork-driving position being sufficiently close to distal ends of the tines to prevent floss contact with user gums thereby preventing gum injury from over-travel of the fork, wherein the bite member is urged to the neutral position by a leaf spring.

9. The device as defined in claim 8, wherein the bite member is pivotally supported.

10. The device as defined in claim 8, wherein the bit member is pivotally supported.

11. A flosser comprising:

a frame;

a pair of spaced tines connected to the frame for supporting a floss span between the tines near distal ends thereof in order to floss teeth; and a bite member movably supported between the tines for moving relative to the tines between a fork-driving position wherein the bite member is sufficiently close to the distal ends of the tines to prevent floss contact with the gums and a neutral position, the bite member being moved into the fork-driving position by a user biting on the bite member with a user tooth located opposite the floss span to drive the floss span through a tight interdental gap, the bite member in the neutral position being sufficiently distant from the distal ends of the tines to allow unimpeded flossing of teeth.

12. The flosser as defined in claim 11, wherein the bite member in the fork-driving position is sufficiently close to the distal ends of the tines to prevent floss contact with user gums thereby preventing gum injury from over-travel of the tines.

13. The flosser as defined in claim 11, wherein the bite member is pivotally supported.

14. The flosser as defined in claim 11, wherein the bite member is slidably supported.

15. A flosser comprising:

a frame;

a pair of tines supported on the frame, each tine having a distal end portion for supporting a floss span between the tines in order to floss teeth; and a bite member having a bite surface supported between the tines such that a user biting on the bite surface can drive the floss span through a tight gap between teeth, the bite member having a stop guard opposite the bite surface for engaging a user tooth opposite the tooth which bites the bite surface thereby limiting travel of the floss span between teeth to avoid driving the span into gums of the user, wherein the bite member is capable of moving relative to the tines to a neutral position sufficiently distant from distal ends of the tines to allow unimpeded flossing of teeth at the gum line of the user.

16. The flosser as defined in claim 15, wherein the bite member is pivotally connected to the frame.

17. The flosser as defined in claim 15, wherein the bite member is slidably supported on the tines.

18. The device as defined in claim 15 wherein the bite member is urged to the neutral position by a spring.

19. The device as defined in claim 15, wherein the bite member is urged to the neutral position by a leaf spring.

20. The flosser as defined in claim 15, wherein the bite surface is slip-resistant.

21. A method of driving a span of floss supported between tines of a fork through a tight interdental gap comprising the steps of:

movably supporting a bite member between the fork tines to allow up and down movement of the bite member and fork relative to each other, the bite member having a bite surface on one side and a stop guard surface on an opposite side;

biting the bite surface of the bite member to cause the bite member to force the fork to drive the floss span through the interdental gap; and preventing over-travel of the span of floss by engaging the stop guard surface of the bite member with a tooth adjacent to the span of floss.

* * * * *

UNITED STATES PATENT AND TRADEMARK OFFICE
CERTIFICATE OF CORRECTION

PATENT NO. : 5,722,440
DATED : March 3, 1998
INVENTOR(S) : Charles L. Urso

It is certified that error appears in the above-identified patent and that said Letters Patent is hereby corrected as shown below:

Column 5, line 7, claim 10: delete "bit" and insert --bite--;

Column 5, line 8, claim 10: delete "pivotally" and insert --slidably--.

Signed and Sealed this

Ninth Day of March, 1999

Attest:

Attesting Officer

Q. TODD DICKINSON

Acting Commissioner of Patents and Trademarks